United States Patent
Helkowski et al.

(10) Patent No.: US 9,931,490 B2
(45) Date of Patent: *Apr. 3, 2018

(54) CONTROL SYSTEM FOR ARTERIAL CATHETER

(71) Applicant: ZOLL CIRCULATION, INCORPORATED, San Jose, CA (US)

(72) Inventors: Richard A. Helkowski, Redwood City, CA (US); Mark Glenn Mitchell, San Jose, CA (US)

(73) Assignee: ZOLL CIRCULATION, INCORPORATED, San Jose, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 14/108,851

(22) Filed: Dec. 17, 2013

(65) Prior Publication Data
US 2015/0165173 A1 Jun. 18, 2015

(51) Int. Cl.
*A61M 29/00* (2006.01)
*A61M 25/10* (2013.01)
*A61M 25/00* (2006.01)

(52) U.S. Cl.
CPC ........... *A61M 25/10184* (2013.11); *A61M 2025/0002* (2013.01); *A61M 2025/1052* (2013.01)

(58) Field of Classification Search
CPC ........... A61M 29/02; A61M 25/10184; A61M 29/00; A61M 25/00; A61M 25/10; A61M 2025/1052; A61B 5/0059; A61B 5/201
See application file for complete search history.

(56) References Cited

U.S. PATENT DOCUMENTS

| | | | |
|---|---|---|---|
| 5,842,996 A | * | 12/1998 | Gruenfeld ............ A61B 17/135 600/490 |
| 6,146,370 A | | 11/2000 | Barbut |
| 6,161,547 A | | 12/2000 | Barbut |
| 6,165,199 A | | 12/2000 | Barbut |

(Continued)

FOREIGN PATENT DOCUMENTS

EP 2353501 8/2001

OTHER PUBLICATIONS

Richard A. Helkowski, Mark Glenn Mitchell, "Control System for Arterial Catheter", related U.S. Appl. No. 14/109,023, Final Office Action dated Jun. 13, 2016.

(Continued)

*Primary Examiner* — Victor Nguyen
(74) *Attorney, Agent, or Firm* — John L. Rogitz

(57) ABSTRACT

A control system for an arterial catheter operable to selectively impede blood flow includes a processor and a storage medium accessible to the processor that bears instructions which when executed by the processor cause the processor to execute logic including receiving a first signal representing a physical parameter associated with a patient in whom the catheter is disposed, receiving a second signal representative of time, and causing inflation of a first balloon on the catheter to impede blood flow in the first artery. Based at least in part on the first signal satisfying a first condition, the instructions include causing deflation of the first balloon. Based at least in part on the second signal indicating elapse of a predetermined time period, the instructions include causing deflation of the first balloon regardless of whether the first signal satisfies the first condition.

10 Claims, 11 Drawing Sheets

(56) References Cited

U.S. PATENT DOCUMENTS

| | | |
|---|---|---|
| 6,217,552 B1 | 4/2001 | Barbut et al. |
| 6,231,551 B1 | 5/2001 | Barbut |
| 6,355,010 B1 | 3/2002 | Barbut |
| 6,383,172 B1 | 5/2002 | Barbut |
| 6,530,894 B1 | 3/2003 | Barbut |
| 6,533,800 B1 | 3/2003 | Barbut |
| 6,555,057 B1 | 4/2003 | Barbut et al. |
| 6,565,552 B1 | 5/2003 | Barbut |
| 6,595,963 B1 | 7/2003 | Barbut |
| 6,595,980 B1 | 7/2003 | Barbut |
| 6,643,415 B1 | 11/2003 | Fukai et al. |
| 6,743,196 B2 | 6/2004 | Barbut et al. |
| 6,830,579 B2 | 12/2004 | Barbut |
| 6,848,448 B1 | 2/2005 | St. Germain et al. |
| 6,887,227 B1 | 5/2005 | Barbut |
| 6,942,686 B1 | 9/2005 | Barbut et al. |
| 7,340,298 B1 | 3/2008 | Barbut |
| 7,371,067 B2 | 5/2008 | Anderson et al. |
| 7,452,352 B2 | 11/2008 | Barbut |
| 7,635,376 B2 | 12/2009 | Barbut |
| 7,643,153 B2 * | 1/2010 | de Boer ............ A61B 5/0059 356/479 |
| 7,867,195 B2 | 1/2011 | Barbut et al. |
| 7,927,268 B1 | 4/2011 | St. Germain et al. |
| 7,993,324 B2 | 8/2011 | Barbut |
| 8,075,584 B2 | 12/2011 | Barbut |
| 8,137,374 B2 | 3/2012 | Barbut |
| 8,221,383 B2 | 7/2012 | Barbut |
| 2006/0206029 A1 | 9/2006 | Yair |
| 2007/0135793 A1 | 6/2007 | Barbut et al. |
| 2007/0233170 A1 | 10/2007 | Gertner |
| 2007/0239135 A9 | 10/2007 | Barbut |
| 2008/0262467 A1 | 10/2008 | Humphrey et al. |
| 2009/0105799 A1 * | 4/2009 | Hekmat ............ A61B 5/201 623/1.11 |
| 2009/0137968 A1 | 5/2009 | Rottenberg |
| 2010/0094330 A1 | 4/2010 | Barbut |
| 2011/0106132 A1 | 5/2011 | Barbut et al. |
| 2012/0089167 A1 | 4/2012 | Barbut |
| 2015/0165174 A1 * | 6/2015 | Helkowski ...... A61M 25/10184 606/194 |

OTHER PUBLICATIONS

Richard A. Helkowski, Mark Glenn Mitchell, "Control System for Arterial Catheter", related U.S. Appl. No. 14/109,023, Applicant's response to Final Office Action filed Sep. 13, 2016.

Richard A. Helkowski, Mark Glenn Mitchell, "Control System for Arterial Catheter", related U.S. Appl. No. 14/109,023, Non-Final Office Action dated Dec. 3, 2015.

Richard A. Helkowski, Mark Glenn Mitchell "Control System for Arterial Catheter", related U.S. Appl. No. 14/109,023, Applicant's response to Non-Final Office Action dated Mar. 3, 2016.

Richard A. Helkowski, Mark Glenn Mitchell, "Control System for Arterial Catheter", related pending application PCT/US2014/061743, Notification Concerning Transmittal of International Preliminary Report on Patentability dated Jun. 30, 2016.

* cited by examiner

CONTROL SYSTEM FOR ARTERIAL CATHETER

This application incorporates by reference in its entirety U.S. patent application Ser. No. 12/639,901 (now U.S. Pat. No. 8,137,374), filed Dec. 16, 2009.

I. FIELD OF THE INVENTION

The present application relates generally to control systems for arterial catheters.

II. BACKGROUND

As recognized in the above-referenced U.S. Pat. No. 8,137,374, incorporated herein by reference in its entirety, selectively blocking certain arteries for limited time can result in reversal of blood flow through other arteries for therapeutic purposes. As understood herein, automating some or all of the inflation protocol can provide additional advantages.

SUMMARY OF THE INVENTION

It is to be understood that placement of balloons on a catheter in accordance with present principles is not limited to, but can be in/on catheter positions described in U.S. Pat. No. 8,137,374 and that any of the occludes and/or constrictors described therein may be used in accordance with present (e.g. balloon) principles.

Accordingly, a control system for an arterial catheter operable to selectively impede blood flow in a first artery to increase blood flow in a second artery includes at least one processor, and at least one computer readable storage medium accessible to the processor. The computer readable storage medium bears instructions which when executed by the processor cause the processor to execute logic including receiving a first signal representing a physical parameter associated with a patient in whom the catheter is disposed, receiving a second signal representative of time, and causing inflation of a first balloon on the catheter to impede blood flow in the first artery. Based at least in part on the first signal satisfying a first condition, the instructions include causing deflation of the first balloon. Based at least in part on the second signal indicating elapse of a predetermined time period, the instructions include causing deflation of the first balloon regardless of whether the first signal satisfies the first condition.

In some embodiments, the first artery is a femoral artery and the second artery is a carotid artery. Also in some embodiments, the physical parameter may include blood pressure of the patient, pressure internal to the first balloon, amount of blockage of the first artery by the first balloon, and/or blood flow rate through the first artery.

Furthermore, in some embodiments, the catheter may include a second balloon, and the logic executed by the processor when accessing the instructions may further include inflating the second balloon and, based at least in part on the first signal satisfying a condition, causing deflation of the second balloon. The instructions may also include, based at least in part on the second signal indicating elapse of a predetermined time period, causing deflation of the second balloon regardless of whether the first signal satisfies the second condition.

Even further, if desired in some embodiments in the first and second balloons may be inflated simultaneously with each other while in other embodiments the first balloon is inflated before inflating the second balloon. In embodiments where the first balloon is inflated before inflating the second balloon, the first balloon may be distal to the second balloon but can also be proximal to the second balloon.

In another aspect, a control system for an arterial catheter operable to selectively impede blood flow in a first artery to increase blood flow in a second artery includes at least one processor, and at least one computer readable storage medium accessible to the processor. The computer readable storage medium bears instructions which when executed by the processor cause the processor to execute logic including receiving a first signal representing a physical parameter associated with a patient in whom the catheter is disposed, receiving a second signal representative of time, and causing inflation of a first balloon on the catheter to impede blood flow in the first artery. Based at least in part on the second signal indicating elapse of a predetermined time period, the instructions include causing deflation of the first balloon. Based at least in part on the first signal satisfying a first condition, the instructions include causing deflation of the first balloon regardless of whether the second signal indicates the elapse of the predetermined time period.

In still another aspect, a method includes receiving, at a control system for an arterial catheter operable to selectively impede blood flow in a first artery to increase blood flow in a second artery, a first signal representing a physical parameter associated with a patient in whom the catheter is disposed. The method also includes receiving a second signal representative of time and causing inflation of a first balloon on the catheter to impede blood flow in the first artery. Based at least in part on the first signal satisfying a first condition, the method includes causing deflation of the first balloon. Based at least in part on the second signal indicating elapse of a predetermined time period, the method includes causing deflation of the first balloon.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
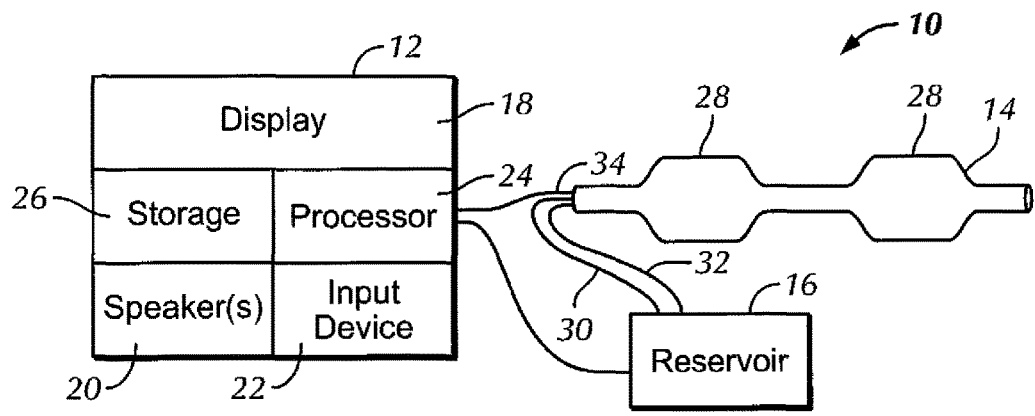
FIGS. 1-5 are block diagrams of example catheter systems in accordance with present principles.

Referring initially to FIG. 1, an exemplary system 10 includes a catheter control system 12, a catheter 14, and a reservoir 16 (sometimes referred to herein as a "fluid source"). First describing the catheter control system 12, it includes a (e.g., touch-enabled) display 18 and one or more speakers 20 for outputting audio such as audible alerts in accordance with present principles. The catheter control system 12 also includes and at least one input device 22 such as, e.g., an audio receiver/microphone, keypad, touchpad, etc. for providing input and/or commands to a processor 24 (processors sometimes referred to herein as "controllers") in accordance with present principles (e.g., to provide input according to the UM of FIGS. 13-19). Note that the processor 24 is understood herein as being configured for controlling the catheter control system 12 in accordance with present principles and indeed the operations of the system 10.

In addition to the foregoing, the catheter control system 12 also may also include a network interface (not shown) for communication over at least one network (also not shown) such as the Internet, an WAN, a LAN, etc. under control of the processor 24 to e.g. communicate with another device such as a computer to e.g. provide alerts, status updates, and catheter information concerning the catheter control system 12 as disclosed herein to the other computer (e.g. a computer at a nurse's station separate from a patient's room in which the system 10 is disposed). In any case, such a network interface may be, e.g., a wired or wireless modem or router, or other appropriate interface such as, e.g., a wireless telephony transceiver. In addition to the foregoing, the catheter control system 12 includes a tangible computer readable storage medium 26 such as disk-based or solid state storage. The medium 26 is understood to store the software code and/or logic discussed herein for execution by the processor 24 in accordance with present principles.

Now in reference to the catheter 14, it is to be understood that the exemplary catheter 14 may be in fluid communication with the reservoir 16 to inflate and/or deflate one or more balloons 28 on the catheter 14 in accordance with present principles via e.g. supply lumen 30 and return lumen 32, and also to supply fluid and/or gas to other portions of the catheter 14 in accordance with present principles. It is to be understood that the reservoir 16, though shown as being separate from the catheter control system 12, may in some embodiments form part of the system 12 and/or be (e.g. mechanically) coupled thereto. The catheter 14 may also be in (e.g. electrical) communication with the control system 12, either wireless (e.g., using respective transmitters/receivers on the control system 12 and catheter 14 not shown) or wired via the exemplary wire 34 shown for control of the catheter 14 by the control system 12 and/or for transmitting inputs between the catheter 14 and control system 12 (e.g., such as the biometric parameter data/input disclosed herein). Also note that the reservoir 16 may be in (e.g. electrical) communication with the control system 12 so that the control system 12 may control the reservoir 16 and supply of fluid to the catheter 14 in accordance with present principles.

Figure 2:
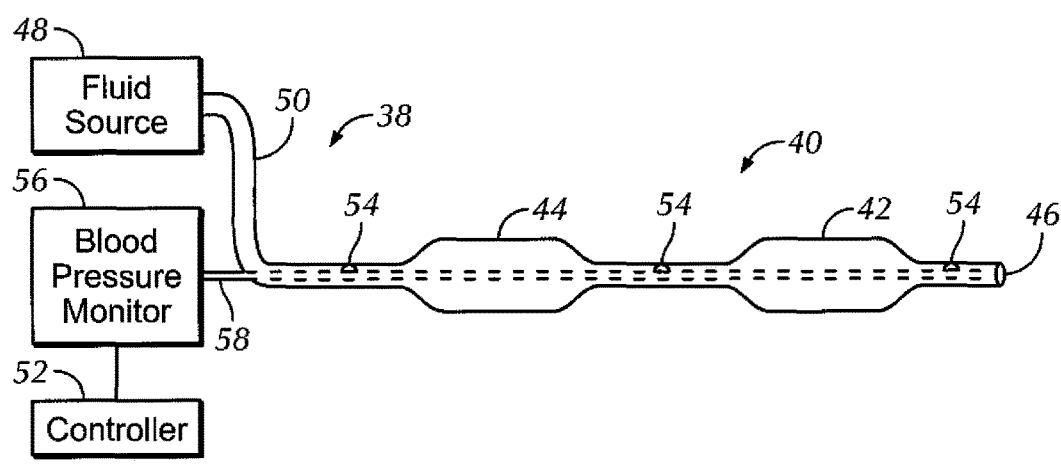

Additionally, before moving on to FIG. 2 it is to be understood that the catheter 14 (including its configuration and its fluid and electrical communication with the control system 12 and reservoir 16) may be any of the catheters described herein and those incorporated by reference as set forth above. Thus, it is to be understood that the system 10 is exemplary and may be used in accordance with the principles and systems disclosed herein (as may any of the catheters/catheter systems disclosed herein or incorporated by reference). Thus, for example, even though not specifically shown in reference to FIGS. 2-5, one or more elements described in reference to FIG. 1 but omitted from FIGS. 2-5 may nonetheless be included in the systems of FIGS. 2-5 though not specifically shown for clarity. Furthermore, it is to be understood that the controllers and/or processors described herein are configured for executing the logic described herein. Also note that as used herein, "proximal" and "distal" in reference to the catheter are understood to be relative to the system 12.

Additionally, note that although a single supply lumen 30 and return lumen 32 are shown, it is to be understood that in some embodiments each of the balloons 28 may be separately and/or independently controlled (e.g. inflated and deflated) such that e.g. the balloons need not necessarily be in fluid communication with each other and both may be connected to their own respective supply and return lumens. Thus, there being two balloons 28 shown in exemplary FIG. 1, in some embodiments four lumens may be employed in such a two-balloon configuration, a first supply lumen and a first return lumen both communicating only with a first of the two balloons, and a second supply lumen and a second return lumen both communicating only with a second of the two balloons. Notwithstanding, also note that in exemplary embodiments a single lumen may act as both a supply lumen and return lumen, either for both balloons or for a single one of the balloons should they be independently controlled in accordance with present principles.

Now describing FIG. 2, an exemplary system 38 including an exemplary catheter 40 is shown. The catheter 40 includes a distal balloon 42, a proximal balloon 44, and a distal tip 46. A fluid source 48 is also shown and is understood to be in fluid communication with the catheter 40 via the supply/return line(s) 50 to e.g. inflate the balloons 42, 44. A controller 52 is also show for executing logic in accordance with present principles to thus e.g. control the catheter and/or inflation and deflation of the balloons 42, 44. The controller 52 is also understood to be configured for receiving input from a blood pressure monitor 56 that itself receives blood pressure input from one or more blood pressure sensors 54 (e.g. when the catheter 40 is disposed in an artery of a patient) electrically connected to the blood pressure monitor 56 to provide input thereto via e.g. at least one blood pressure line 58 extending longitudinally through at least a portion of the catheter 40 and between the sensor(s) 54 and monitor 56.

As may be appreciated from FIG. 2, the sensor(s) 54 may be disposed against, along, or proximate to an inner side of a catheter wall of the catheter 40 that also includes an outer side e.g. in fluid contact with a patient's blood so that the sensor(s) 54 may thus sense blood pressure through the wall of the catheter. Alternatively or in addition to sensing blood pressure though the catheter wall, the catheter wall may include a port(s) so that the sensor(s) 54 may be positioned at or proximate to the port to thus be in fluid contact with the blood of a patient when disposed in the patient's artery to thereby sense blood pressure. Furthermore, note that the sensors 54 shown in FIG. 2 are shown as being disposed longitudinally along portions of the catheter 40 that do not also include one of the balloons 42, 44 disposed there along and in some instances are thus disposed along the catheter 40 at portions between the balloons 42, 44. Nonetheless, note that if desired one of more blood pressure sensors may be disposed longitudinally along a portion of the catheter including the balloon and may even be positioned within the balloon itself so that blood pressure may be sensed through a balloon wall in accordance with present principles.

Figure 3:
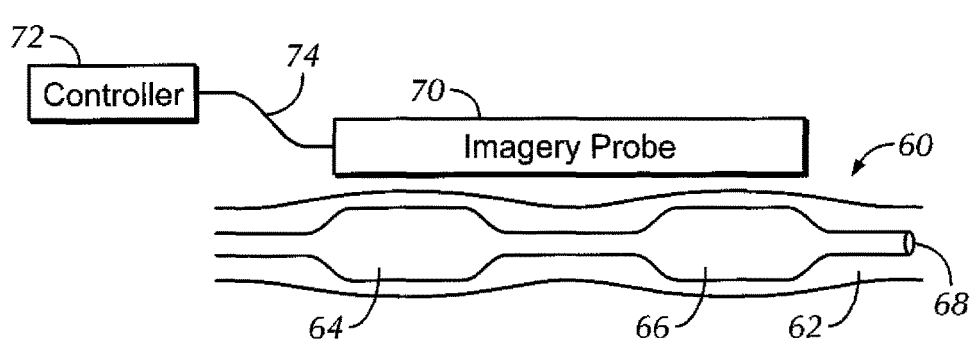

Now addressing FIG. 3, a catheter 60 is shown as being disposed in an vessel/artery 62 of a patient in accordance with present principles. The catheter 60 includes a proximal balloon 64, a distal balloon 66, and a distal tip 68. Also shown in an imagery probe 70 understood to be disposed within or proximate to the patient (e.g. but not inside the artery 62). The probe 70 is electrically connected to a controller 72 to provide input thereto via a line 74. Thus, in accordance with present principles, the imagery probe 70 may be positioned in or near the patient at or proximate to the artery 62 such that occlusion (e.g., partial or full) of the artery 62 may be determined by the controller 72 based on imagery from the probe 70. The controller 72 may thus provide an indication of occlusion (e.g. on a display such as the display 18 described above) in a percentage parameter (e.g. the amount of occlusion indicated as a percentage). The probe 70 may be, for example, an ultrasonic probe, or it may be a probe that senses radiopaque dye that has been injected either into the patient's bloodstream, or alternatively into the balloons, or it may be another appropriate imaging probe.

Figure 4:
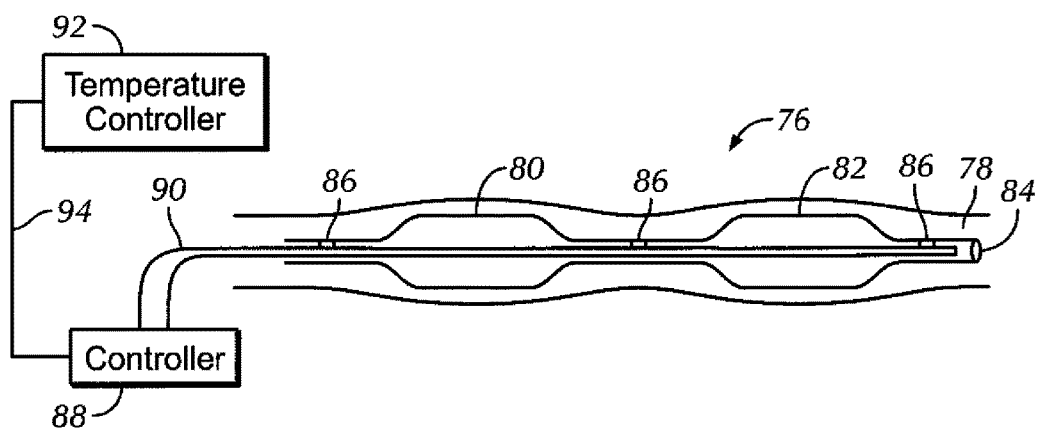

Continuing the detailed description in reference to FIG. 4, a catheter 76 is shown as being disposed in an vessel/artery 78 of a patient in accordance with present principles. The catheter 76 includes a proximal balloon 80, a distal balloon 82, and a distal tip 84. Also shown are temperature and/or flow rate sensors 86 disposed against, along, or proximate to an inner side of a catheter wall of the catheter 76 that also includes an outer side e.g. in fluid contact with a patient's blood in the artery 78 so that the sensors 86 may gather input/measurements (e.g. temperature and/or blood flow rate) regarding cardiac output in accordance with present principles and provide the measurements to a controller 88 electrically connected thereto via line 90 extending longitudinally along the catheter 76, it being understood that the controller 88 is also electrically connected to temperature controller 92 via line 94.

Thus, for example, cardiac output (e.g. blood flow) may be measured using a temperature differential between two or more temperature signals from sensors 86 disposed along different portions of the catheter 76 and accordingly e.g. blood flow may be inversely proportional to the temperature differential/change in temperature. Nonetheless, note that ports may also be included on the catheter 76 along portions of the catheter wall where the sensors 86 are disposed such that the sensors 86 may be in fluid contact with the patient's blood via the ports to gather measurements in accordance with present principles. Further note that in embodiments where blood passes through e.g. a portion of the catheter 76 itself, measurements may be taken by the sensors according to temperature/flow within the portion (it being understood that similar observations apply to the measurements gathered using the catheter 40 described above as well).

Figure 5:
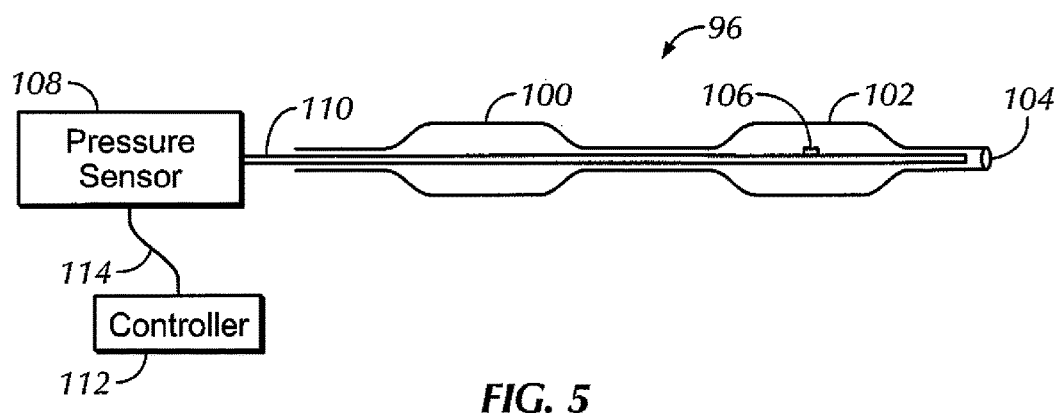

Now addressing FIG. 5, yet another exemplary catheter 96 is shown. The catheter 96 includes a proximal balloon 100, a distal balloon 102, and a distal tip 104. Also shown is at least one sensors 106 located inside a balloon(s) such as the distal balloon 104 for measuring (e.g. interior/internal) balloon pressure of the balloon in which the sensor 106 is disposed. The one or more sensors 106 are thus electrically connected to a pressure sensor unit 108 via line 110 that extends longitudinally along at least an inner portion of the catheter 96 to provide input thereto, where the pressure sensor unit 108 is itself electrically connected to a controller 112 via a line 114 for providing input thereto on balloon pressure (e.g. for the controller 112 to configure the catheter 96 and specifically one or more of the balloons for a desired inflation pressure, artery occlusion, and/or to address a catheter leak and/or to prevent the balloon from bursting or rupturing). Each balloon can have its own internal pressure sensor.

Figure 6:
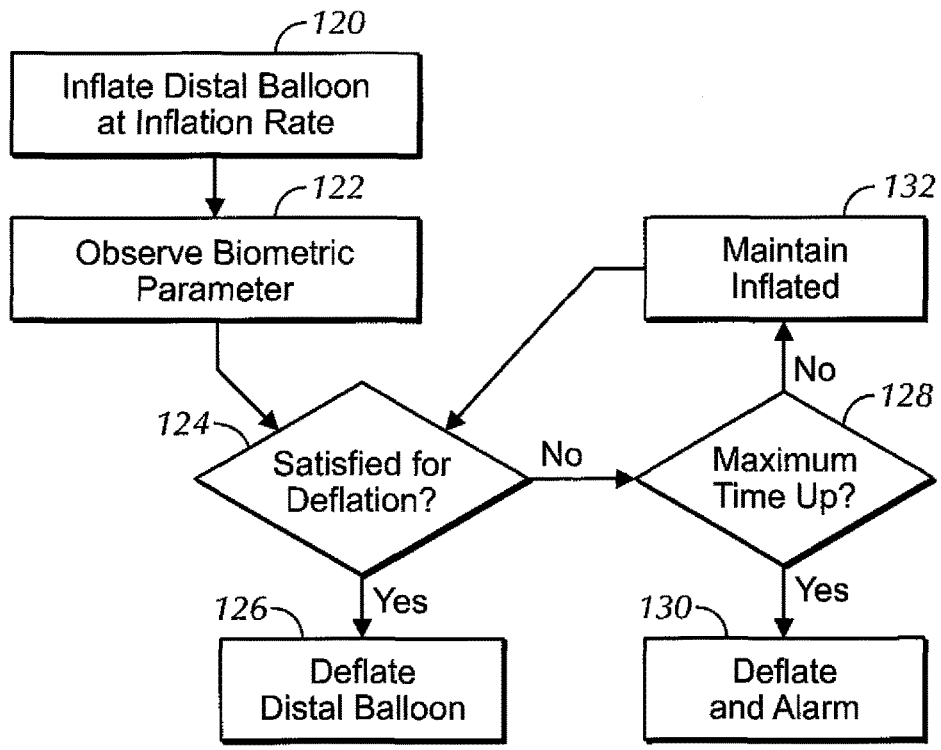
FIGS. 6-12 are exemplary flowcharts of logic to be executed by catheter systems in accordance with present principles.

Continuing the detailed description in reference to FIG. 6, an exemplary flow chart of logic for inflating at least a distal balloon of a catheter in accordance with present principles is shown. Beginning at block 120, the distal balloon is inflated at an (e.g. constant or pulsed) inflation rate. Then at block 122 the logic observes and/or monitors at least one biometric parameter such as those discussed above (e.g., blood pressure, vessel occlusion, cardiac output, interior balloon pressure, etc.). Thereafter, at decision diamond 124, the logic determines whether at least one of the biometric parameters has been satisfied—e.g., that it is out of (e.g., above or below) an acceptable, preferred, and/or normal level or range (e.g. as input by a physician to the system processor). If a positive determination is made at diamond 124, the logic moves to block 126 where the logic deflates the distal balloon and even provides an alarm (e.g. a visual alarm via a display such as the display 18 described above and/or audible alarm such as a bell or emergency tone via a speaker such as the speaker 20 described above). If, however, a negative determination is made at diamond 124, the logic instead proceeds to decision diamond 128.

At diamond 128, the logic determines whether a maximum time (e.g. threshold) has been reached/satisfied for inflation of the distal balloon (e.g. either or both of the maximum time that inflation is permitted or safe, and/or the maximum time that the balloon is permitted to remain inflated once a desired inflation pressure has been reached). If a positive determination is made at diamond 128, then the logic proceeds to block 130 where the logic deflates the distal balloon and even provides an alarm as set forth above regardless of whether one or more biometric parameters are satisfied. If, however, a negative determination is made at diamond 128, the logic instead moves to block 132 where the balloon inflation is maintained. The logic then reverts back to diamond 124 thereafter and proceeds from diamond 124.

Figure 7:
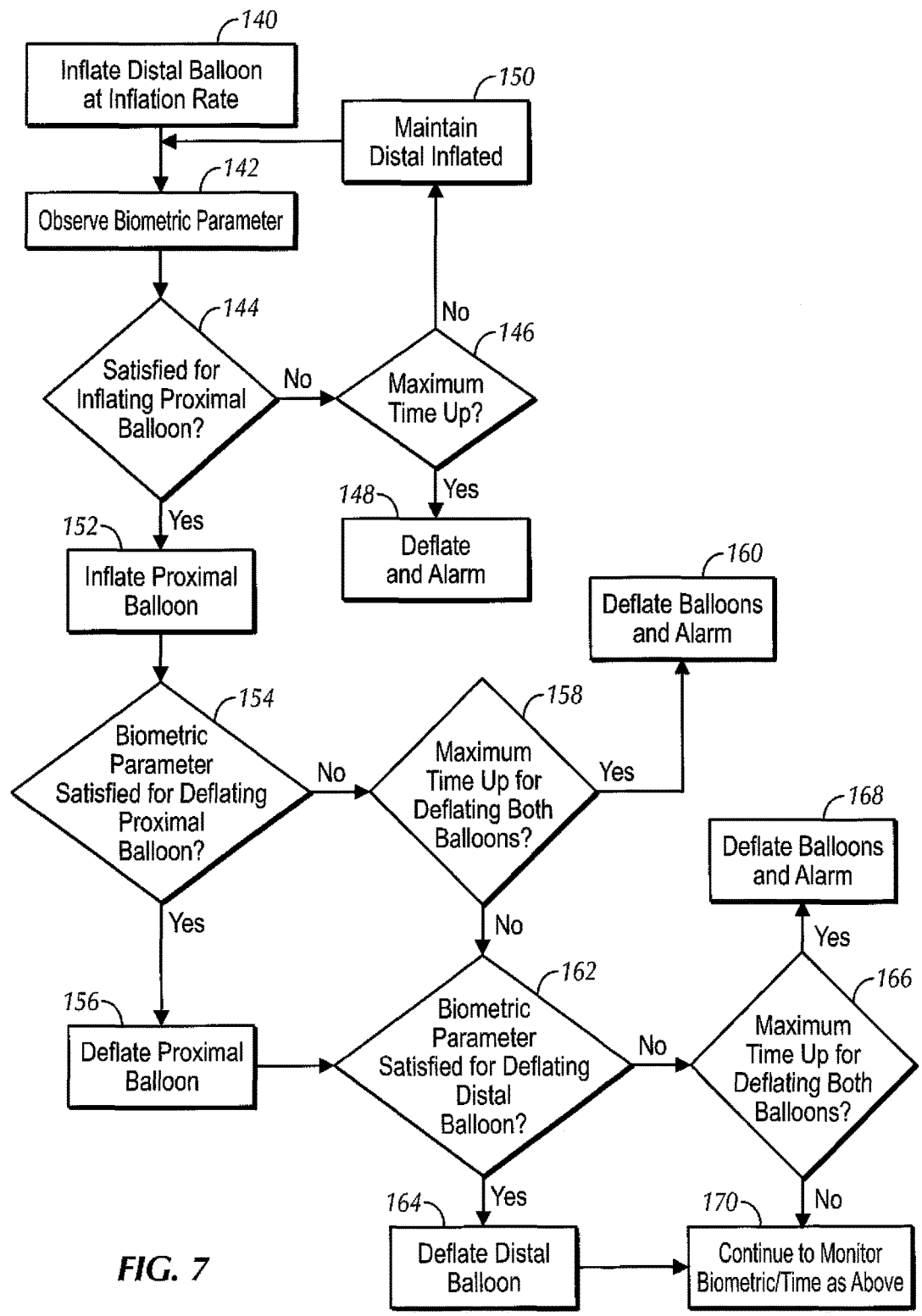

Now addressing FIG. 7, an exemplary flow chart of logic for inflating proximal and distal balloons of a catheter in accordance with present principles is shown. Beginning at block 140, the distal balloon of a catheter is inflated at an inflation rate. The logic then moves to block 142 where the logic observes and/or monitors at least one biometric parameter such as those discussed above. Thereafter, the logic moves to decision diamond 144 where the logic determines whether the at least one of the biometric parameters has been satisfied for inflating the proximal balloon of the catheter. If at diamond 144 the logic determines that the at least one biometric parameter has not been satisfied for inflating the proximal balloon (e.g. a condition exists based on the biometric parameter where it is not appropriate/safe to inflate the proximal balloon), the logic moves to decision diamond 146.

At diamond 146, the logic determines whether a maximum time (e.g. threshold) has been reached/satisfied for inflation of the distal balloon (e.g. either or both of the maximum time that inflation is permitted or safe, and/or the maximum time that the balloon is permitted to remain inflated once a desired inflation has been reached) regardless of whether a biometric parameter for the proximal balloon has been satisfied. If a positive determination is made at diamond 146, then the logic proceeds to block 148 where the logic deflates distal balloon and provides an alarm as set forth above. If, however, a negative determination is made at diamond 146, the logic instead moves to block 150 where the balloon inflation is maintained. The logic then reverts back to block 142 from block 150 and proceeds accordingly.

Continuing in reference to FIG. 7 but referring back to decision diamond 144 for deciding whether at least one biometric parameter has been satisfied for inflating the proximal balloon, should a positive rather than a negative determination be made thereat, the logic proceeds to block 152 instead of decision diamond 146. At block 152, the logic thus inflates the proximal balloon of the catheter and then moves to decision diamond 154. At diamond 154 the logic determines whether at least one biometric parameter has been satisfied for deflating the proximal balloon in accordance with present principles. If a positive determination is made, the logic then moves to block 156 where the logic deflates the proximal balloon and then moves to diamond 162, which will be described shortly.

However, before describing diamond 162, reference is again made to decision diamond 154 where, should a negative determination be made rather than a positive one regarding whether at least one biometric parameter has been satisfied for deflating the proximal balloon, the logic instead moves to decision diamond 158. At decision diamond 158, the logic determines whether a maximum time (e.g. threshold) has been reached/satisfied in accordance with present principles for deflating both the proximal and distal balloons (e.g., successively or simultaneously) e.g. regardless of whether a biometric parameter has been satisfied for deflating the proximal balloon or both balloons. If a positive determination is made at diamond 158, the logic proceeds to block 160 and deflates both balloons and provides at least one alarm. If a negative determination is made, the logic instead moves to diamond 162.

At decision diamond 162 and regardless of whether the logic proceeded thereto from block 156 or diamond 158, the logic determines whether at least one biometric parameter has been satisfied for deflating the distal balloon. If a positive determination is made at diamond 162, the logic moves to block 164 where the logic deflates the distal balloon and then moves to block 170, which will be described shortly. However, if a negative determination is made at diamond 162, the logic proceeds to diamond 166 where the logic determines whether a maximum time (e.g. threshold) has been reached/satisfied in accordance with present principles for deflating at least one of the proximal and distal balloons (e.g. regardless of a biometric parameter being satisfied). Note that if the logic proceeded to diamond 166 along a path including block 156, then at diamond 166 the determination involves determining whether to deflate only the distal balloon since the proximal one was deflated at block 156. Also note that if the logic proceeded to diamond 166 along a path including diamond 158, then at diamond 166 the determination involves determining whether to deflate both the proximal and distal balloons because in such a case the logic has yet to deflate either one.

Regardless, if a positive determination is made at diamond 166, the logic proceeds to block 168 where the logic deflates one or both balloons and provides at least one alarm. However, if a negative determination is made at diamond 166, the logic instead moves to block 170. At block 170 and regardless of whether the logic has moved thereto from block 164 or diamond 166, the logic continues to monitor at least one biometric parameter and/or time in accordance with present principles and regardless of the proximal and distal balloon configurations being inflated, deflated, or any combination thereof depending on which path may have been taken in the logic flow of FIG. 7.

Figure 8:
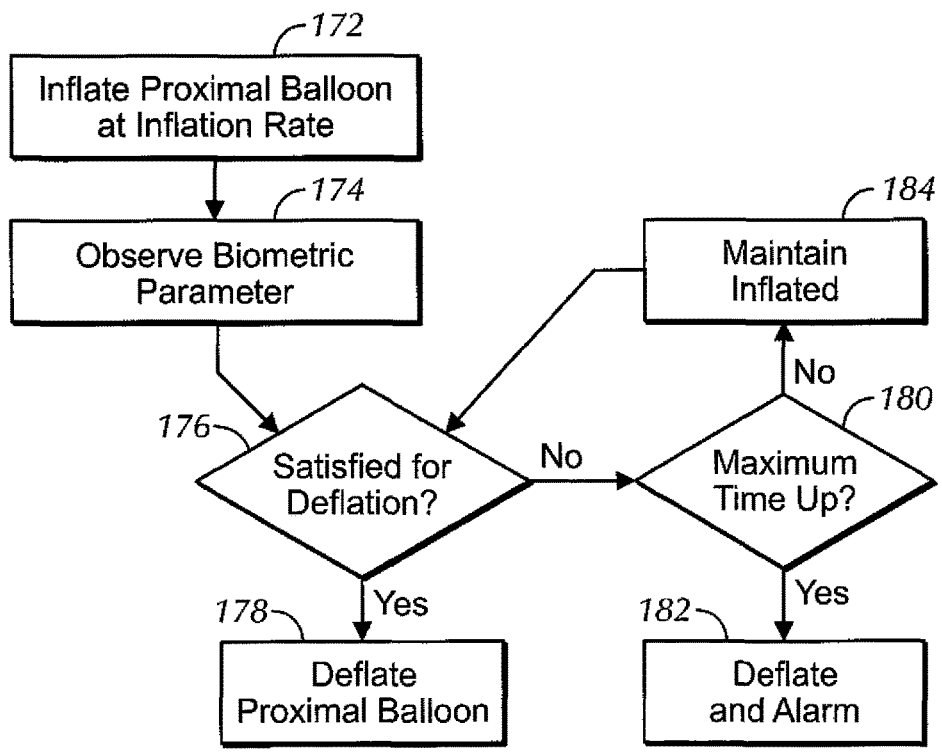

Now in reference to FIG. 8, an exemplary flow chart of logic for inflating at least a proximal balloon of a catheter in accordance with present principles is shown. Beginning at block 172, the proximal balloon is inflated at an (e.g. constant or pulsed) inflation rate. Then at block 174 the logic observes and/or monitors at least one biometric parameter such as those discussed above (e.g., blood pressure, vessel occlusion, cardiac output, interior balloon pressure, etc.). Thereafter, at decision diamond 176, the logic determines whether the at least one of the biometric parameters has been satisfied—e.g., that it is out of (e.g., above or below) an acceptable, preferred, and/or normal level or range. If a positive determination is made at diamond 176, the logic moves to block 178 where the logic deflates the proximal balloon and even provides an alarm (e.g. a visual alarm via a display such as the display 18 described above and/or audible alarm such as a bell or emergency tone via a speaker such as the speaker 20 described above). If, however, a negative determination is made at diamond 176, the logic instead proceeds to decision diamond 180.

At diamond 180, the logic determines whether a maximum time (e.g. threshold) has been reached/satisfied for inflation of the proximal balloon (e.g. either or both of the maximum time that inflation is permitted or safe, and/or the maximum time that the balloon is permitted to remain inflated once a desired inflation has been reached) regardless of the biometric parameter being satisfied. If a positive determination is made at diamond 180, then the logic proceeds to block 182 where the logic deflates the proximal balloon and even provides an alarm as set forth above. If, however, a negative determination is made at diamond 180, the logic instead moves to block 184 where the balloon inflation is maintained. The logic then reverts back to diamond 176 thereafter and proceeds accordingly.

Figure 9:
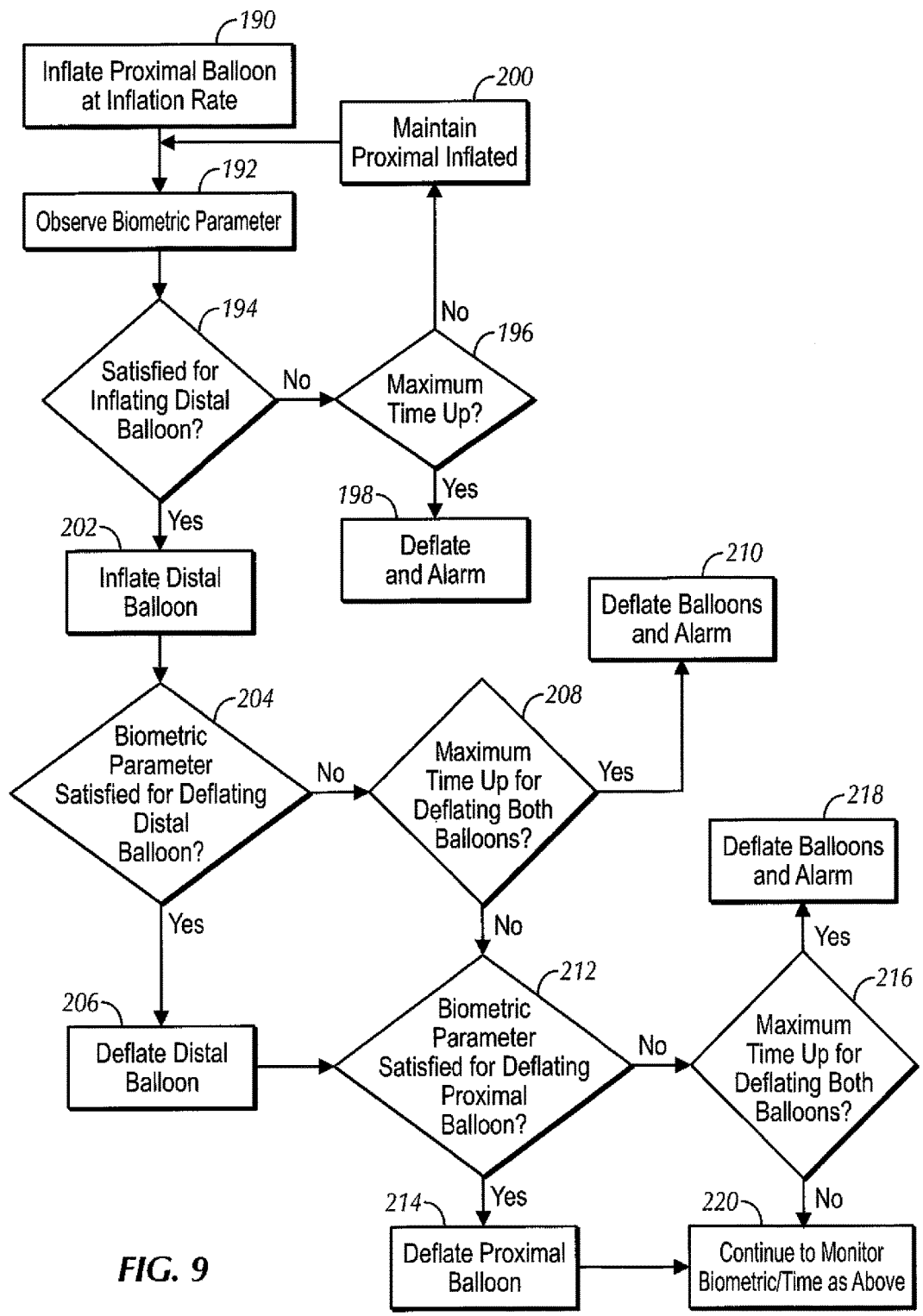

Turning now to the flow chart shown in FIG. 9, an exemplary flow chart of logic for inflating distal and proximal balloons of a catheter in accordance with present principles is shown but, in contrast to FIG. 7, in FIG. 9 the proximal balloon is inflated first. Thus, beginning at block 190, the proximal balloon of a catheter is inflated at an inflation rate. The logic then moves to block 192 where the logic observes and/or monitors at least one biometric parameter such as those discussed above. Thereafter, the logic moves to decision diamond 194 where the logic determines whether the at least one of the biometric parameters has been satisfied for inflating the distal balloon of the catheter. If at diamond 194 the logic determines that the at least one biometric parameter has not been satisfied for inflating the distal balloon (e.g. a condition exists based on the biometric parameter where it is not appropriate/safe to inflate the distal balloon), the logic moves to decision diamond 196.

At diamond 196, the logic determines whether a maximum time (e.g. threshold) has been reached/satisfied for inflation of the proximal balloon (e.g. either or both of the maximum time that inflation is permitted or safe, and/or the maximum time that the balloon is permitted to remain inflated once a desired inflation has been reached). If a positive determination is made at diamond 196, then the logic proceeds to block 198 where the logic deflates the proximal balloon and provides an alarm as set forth above. If, however, a negative determination is made at diamond 196, the logic instead moves to block 200 where the balloon inflation is maintained. The logic then reverts back to block 192 from block 200 and proceeds accordingly.

Continuing in reference to FIG. 9 but referring back to decision diamond 194 for deciding whether at least one biometric parameter has been satisfied for inflating the distal balloon, should a positive rather than a negative determination be made thereat, the logic proceeds to block 202 instead of decision diamond 196. At block 202, the logic thus inflates the distal balloon of the catheter and then moves to decision diamond 204. At diamond 204 the logic determines whether at least one biometric parameter has been satisfied for deflating the distal balloon in accordance with present principles. If a positive determination is made, the logic then moves to block 206 where the logic deflates the distal balloon and then moves to diamond 212, which will be described shortly.

However, before describing diamond 212, reference is again made to decision diamond 204 where, should a negative determination be made rather than a positive one regarding whether at least one biometric parameter has been satisfied for deflating the distal balloon, the logic instead moves to decision diamond 208. At decision diamond 208, the logic determines whether a maximum time (e.g. threshold) has been reached/satisfied in accordance with present principles for deflating both the distal and proximal balloons (e.g., successively or simultaneously) regardless of whether a biometric parameter has been satisfied for deflating the distal balloon or both balloons. If a positive determination is made at diamond 208, the logic proceeds to block 210 and deflates both balloons and provides at least one alarm accordingly. If a negative determination is made, the logic instead moves to diamond 212.

At decision diamond 212 and regardless of whether the logic proceeded thereto from block 206 or diamond 208, the logic determines whether at least one biometric parameter has been satisfied for deflating the proximal balloon. If a positive determination is made at diamond 212, the logic moves to block 214 where the logic deflates the proximal balloon and then moves to block 220, which will be described shortly. However, if a negative determination is made at diamond 212, the logic proceeds to diamond 216 where the logic determines whether a maximum time (e.g. threshold) has been reached/satisfied in accordance with present principles for deflating at least one of the proximal and distal balloons and regardless of a biometric parameter being satisfied. Note that if the logic proceeded to diamond 216 along a path including block 206, then at diamond 216 the determination involves determining whether to deflate only the proximal balloon since the distal one was deflated at block 206. Also note that if the logic proceeded to diamond 216 along a path including diamond 208, then at diamond 216 the determination involves determining whether to deflate both the distal and proximal balloons because in such a case the logic has yet to deflate either one.

Regardless, if a positive determination is made at diamond 216, the logic proceeds to block 218 where the logic deflates one or both balloons accordingly and provides at least one alarm. However, if a negative determination is made at diamond 216, the logic instead moves to block 220. At block 220 and regardless of whether the logic has moved thereto from block 214 or diamond 216, the logic continues to monitor at least one biometric parameter and/or time in accordance with present principles and regardless of the distal and proximal balloon configurations being inflated, deflated, or any combination thereof depending on which path may have been taken in the logic flow of FIG. 9.

Figure 10:
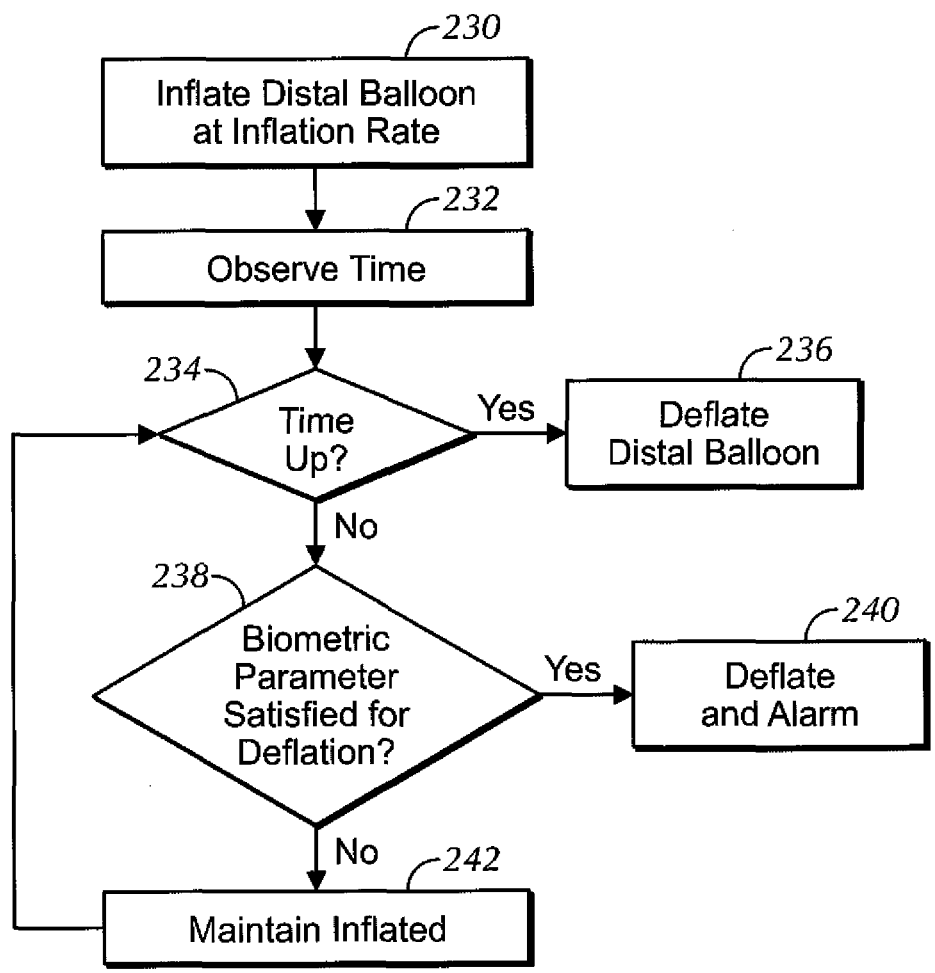

Continuing the detailed description in reference to FIG. 10, an exemplary flow chart of logic for inflating at least a distal balloon of a catheter in accordance with present principles is shown. Beginning at block 230, the distal balloon is inflated at an (e.g. constant or pulsed) inflation rate. Then at block 232 the logic observes and/or monitors time (e.g. based on a threshold) in accordance with present principles, e.g. either time while inflating or total time from the beginning of inflation and continuing after inflation ceases but while the distal balloon is still in an at least partially inflated configuration once a desired inflation has been reached. The logic then moves to decision diamond 234 where the logic determines whether the time(s) described immediately above is "up" in that a determination is made (e.g., the time(s) described herein has transpired and/or expired such that a determination is made) as to whether the distal balloon should be deflated based on the time(s), e.g. as determined by a physician and input to the system executing the present logic. If a positive determination is made the logic then moves to block 236 where the logic deflates the distal balloon and provides at least one alarm in accordance with present principles. However, if a negative determination is made at diamond 234, the logic instead moves to diamond 238.

At diamond 238 the logic determines whether at least one biometric parameter such as those discussed above has been satisfied for deflation (e.g., regardless of whether time(s) is up) in accordance with present principles. If a positive determination is made at diamond 238, the logic proceeds to block 240 where the logic deflates the distal balloon and provides an alarm in accordance with present principles. If, however, a negative determination is made at diamond 238, the logic instead proceeds to block 242 where the distal balloon inflation is maintained. The logic then reverts back to diamond 234 thereafter and proceeds accordingly.

Figure 11:
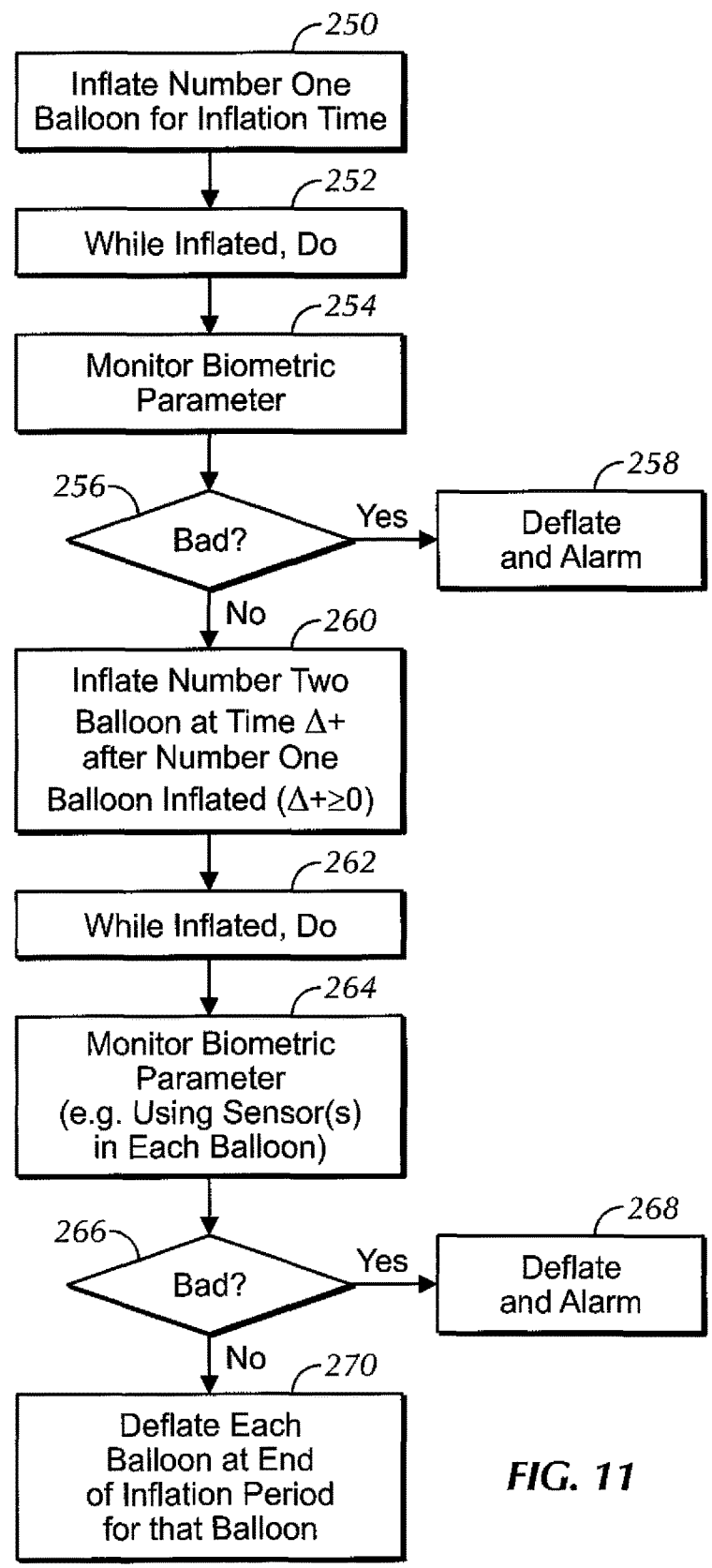

Moving to FIG. 11, yet another flow chart is shown, this one pertaining to inflation and deflation of proximal and distal balloons based on time but also deflating the balloons regardless of time if one or more biometric parameters are satisfied. It is to be understood that as described below, balloon number one may be the proximal balloon of a catheter and balloon number two the distal balloon of a catheter, though present principles recognize that in other embodiments the reverse may be the case in that balloon number one may be the distal balloon while balloon number two may be the proximal balloon. Regardless, the logic of FIG. 11 begins at block 250, the logic inflates balloon number one for an inflation time in accordance with present principles. The logic then moves to block 252 where a do loop is entered while balloon number one is inflated. The logic thereafter proceeds to block 254 where the logic monitors at least one biometric parameter in accordance with present principles, and then moves to decision diamond 256 where the logic determines whether at least one of the at least one monitored biometric parameters is bad in accordance with present principles (e.g. outside of an accepted range for the biometric parameter during which it is still safe and/or preferable that the balloon be inflated).

If a positive determination is made at diamond 256 (e.g., that one of the biometric parameters is outside the acceptable range), then the logic moves to block 258 where the logic deflates balloon number one and provides an alarm in accordance with present principles. However, if a negative determination is made at diamond 256, the logic instead moves to block 260 where the logic inflates balloon number two e.g. after a change in time (e.g. at a time after the first balloon was inflated). Thereafter, the logic proceeds to block 262 where, while both balloons are inflated, a do loop is entered.

The logic then proceeds to block 264 where the logic monitors at least one biometric parameter (e.g. for each balloon using e.g. sensors in each balloon, where the biometric parameter being measured need not be the same type for each balloon but nonetheless may be if desired). After block 264, the logic proceeds to decision diamond 266 where the logic determines whether at least one of the at least one monitored biometric parameters is bad in accordance with present principles (e.g. outside of an accepted range for the biometric parameter during which it is still safe and/or preferable that the balloon be inflated).

If a positive determination is made at diamond 266 (e.g., that one of the biometric parameters is outside the acceptable range), then the logic moves to block 268 where the logic deflates the balloons and provides an alarm in accordance with present principles. However, if a negative determination is made at diamond 266, the logic instead moves to block 270 where the logic maintains inflation of the balloons until such time each balloon should be deflated at the end of a deflation period (e.g. predetermined) for that particular balloon or for both balloons.

Figure 12:
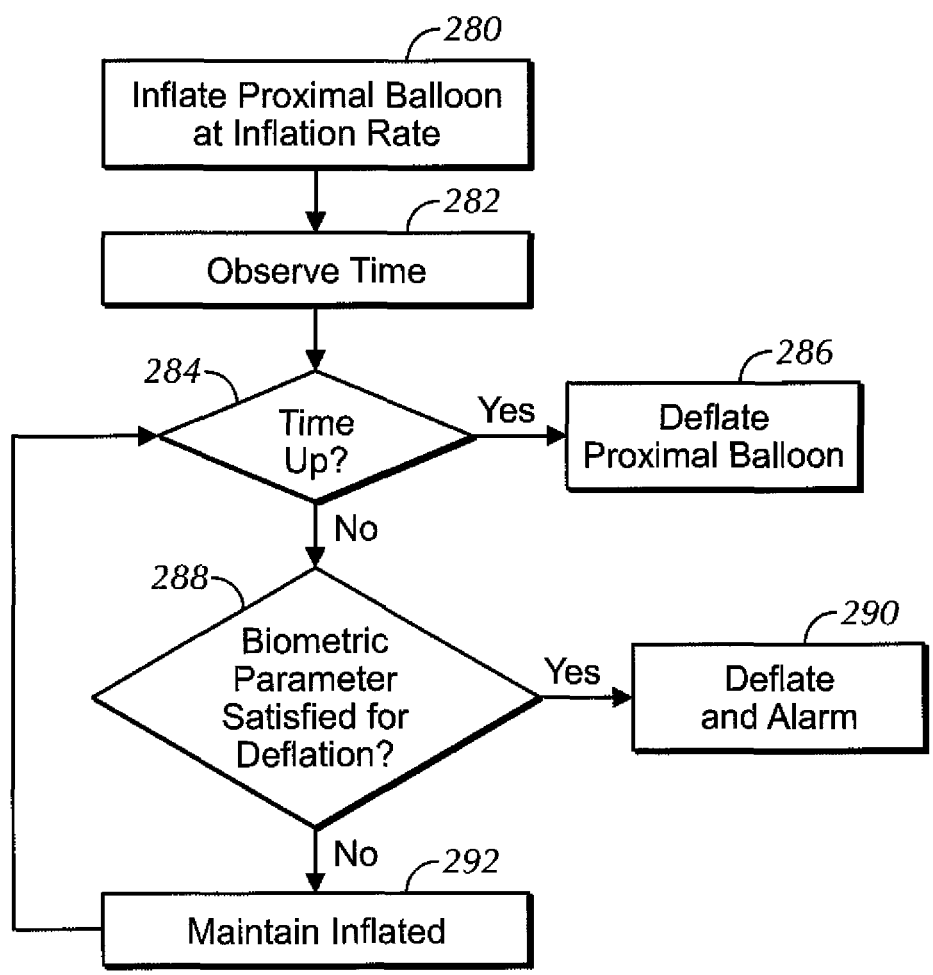

Before moving on to FIG. 12, note that in the context of FIG. 11, time may nonetheless also be monitored as described herein such that one or both of balloons one and two may be deflated based on time regardless of a biometric parameter being satisfied as determined at diamonds 256 and 266. Furthermore, note that in addition to or in lie of making determinations based on biometric parameters at decision diamonds 256 and 266, the determinations at these diamonds may be made based on time (and e.g. after such determinations based on time another determination may be made regardless of time based on one biometric parameter).

Now in reference to FIG. 12, another exemplary flow chart of logic for inflating at least a proximal balloon of a catheter in accordance with present principles is shown. Beginning at block 280, the proximal balloon is inflated at an (e.g. constant or pulsed) inflation rate. Then at block 282 the logic observes and/or monitors time (e.g. based on a threshold) in accordance with present principles, e.g. either time while inflating or total time from the beginning of inflation and continuing after inflation ceases but while the proximal balloon is still in an at least partially inflated configuration once a desired inflation has been reached. The logic then moves to decision diamond 284 where the logic determines whether the time described immediately above is "up" in that a determination is made (e.g., the time(s) described herein has transpired and/or expired such that a determination is made) as to whether the proximal balloon should be deflated based on the time(s), e.g. as determined by a physician and input to the system executing the present logic. If a positive determination is made the logic then moves to block 286 where the logic deflates the proximal balloon and provides at least one alarm in accordance with present principles. However, if a negative determination is made at diamond 284, the logic instead moves to diamond 288.

At diamond 288 the logic determines whether at least one biometric parameter such as those discussed above has been satisfied for deflation (e.g., regardless of whether time is up) in accordance with present principles. If a positive determination is made at diamond 288, the logic proceeds to block 290 where the logic deflates the proximal balloon and provides an alarm in accordance with present principles. If, however, a negative determination is made at diamond 288, the logic instead proceeds to block 292 where the proximal balloon inflation is maintained. The logic then reverts back to diamond 284 thereafter and proceeds accordingly.

Before moving on to FIGS. 13-19, it is to be understood that although not explicitly shown on the face of FIGS. 6-12, present principles recognize that when inflating one or more balloons in accordance with present principles at e.g. an inflation rate, inflation may be stopped once e.g. a specified (e.g., predetermined as input and/or determined by a physician prior to inflation) pressure in the balloon has been reached. Furthermore, present principles recognize that while inflating and/or once the specified inflation level/pressure has been reached, error checking may be performed by the processor executing the logic discussed above to e.g. identify balloon leaks and other mechanical and/or electrical (e.g. computer system) errors, and that upon identification and/or determination of an error, inflation may stop even if before the desired balloon pressure is reached.

Further in reference to FIGS. 6-12 and although not explicitly shown in their face, it is to be understood that balloon inflation may be maintained in between steps of inflating and then deflating the balloons. Thus, e.g., the logic discussed herein may include inflating a balloon in accordance with present principles, then maintaining the current pressure (e.g. reached during inflation) for e.g. a threshold time and/or predetermined time, and then deflating the balloon(s) in accordance with present principles.

Continuing the detailed description in reference to FIGS. 13-19, exemplary user interfaces (UIs) that may be presented on e.g. a display of a catheter system such as the display 18 in accordance with present principles is shown. Thus, it is to be understood that the UIs of FIGS. 13-19 may be used in conjunction with logic executed by a processor such as the processor 24 and as represented by the exemplary flow charts described above to undertake present principles (e.g., the UIs may be manipulated to provide input to a system processor such as the processor 24 to undertake/execute a function in accordance with present principles such as e.g. a distal balloon deflation based on time or user input).

Figure 13:
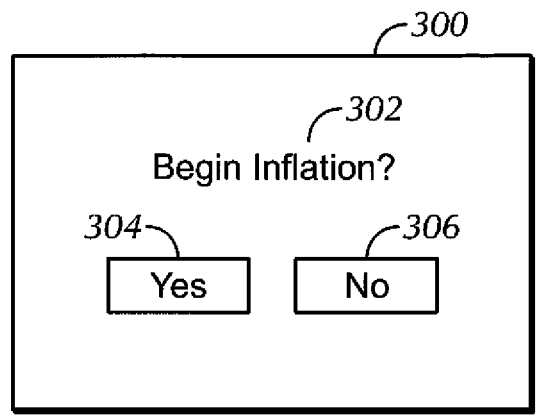
FIGS. 13-19 are exemplary user interfaces (UIs) to be presented on a display of a catheter system in accordance with present principles.

Beginning first with FIG. 13, a UI 300 is shown. The UI 300 includes a prompt 302 regarding whether to begin inflation, along with a yes selector 304 selectable to cause inflation to begin for one or more balloons in accordance with present principles, and a no selector 306 selectable to provide input to the system to not begin inflation.

Figure 14:
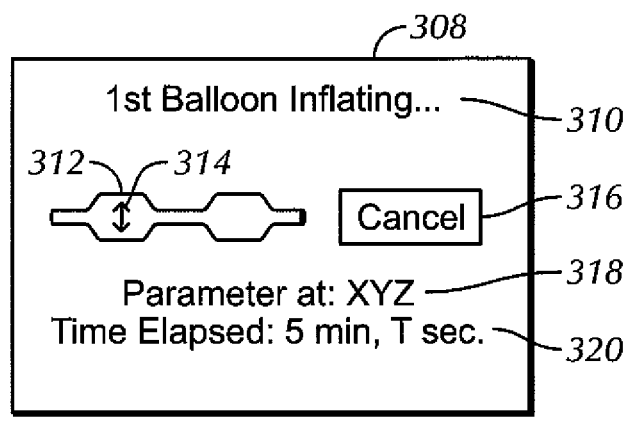

FIG. 14 shows a UI 308 including an indicator 310 that at least a first balloon is inflating. Also shown is a representation 312 of a catheter (e.g. an icon representation) that includes bi-directional arrows 314 vertically disposed within the representation 312 and pointing away from each other (e.g. up and down) to indicate that the first balloon of the representation in which the arrows 314 are disposed is inflating (e.g. in the present instance, indicating that the proximal balloon is inflating). Also shown is a cancel selector element 316 selectable to cancel and/or stop the inflation (e.g., a manual override) and/or to cause the balloon to deflate. Furthermore, the UI 308 includes a parameter indicator 318 indicating a (e.g. current) biometric parameter being monitored in accordance with present principles, and an elapsed time indicator 320 indicating e.g. the time elapsed since the start of the balloon inflation.

Figure 15:
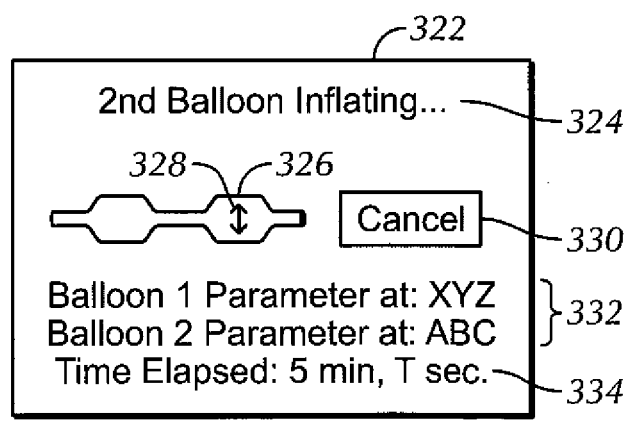

Moving on to FIG. 15, an exemplary UI 322 is shown for indicating that a second balloon of a catheter is inflating in accordance with present principles, in this case the distal balloon, as represented by indicator 324. Also shown is a representation 326 of a catheter that includes bi-directional arrows 328 similar to the arrows 314 described above in that they indicate that a balloon is inflating, in this case the second, distal balloon. A cancel selector element 330 is also shown for canceling and/or stopping inflation of at least the second balloon, but may also be selectable for canceling and/or stopping inflation of both balloons and/or deflating them. Furthermore, the UI 322 includes plural parameter indicators 332 indicating respective (e.g. current) biometric parameters being monitored in accordance with present principles for each of the balloons (though in addition to or in lieu of the foregoing, a cumulative biometric parameter and/or overall biometric parameter may be presented). Also shown is an elapsed time indicator 334 indicating e.g. the time elapsed since the start of the second balloon inflation, but in some instances may indicate the time elapsed since the beginning of inflation of the first balloon.

Figure 16:
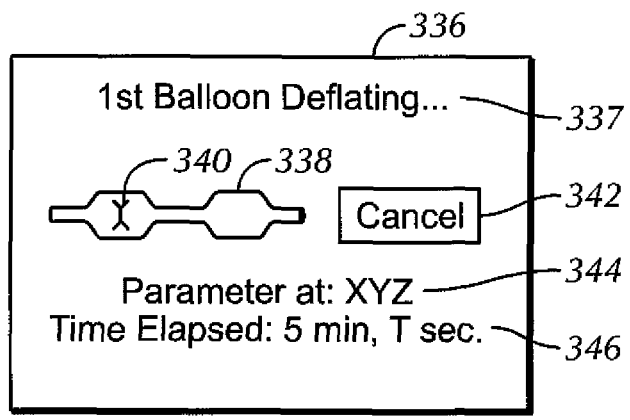

Continuing in reference to FIG. 16, a deflation UI 336 is shown for indicating that the first balloon is deflating, as indicated by indicator 337. Thus, a representation 338 of a catheter includes bi-directional arrows 340 vertically disposed within the representation 338 and pointing toward each other (e.g. down and up toward the middle of the arrow) to indicate that the first balloon is deflating (e.g. in the present instance, indicating that the proximal balloon is deflating). Also shown is a cancel selector element 342 selectable to cancel and/or stop the deflation (e.g., a manual override) to thus maintain an at least partial inflation of the balloon, and/or to cause the balloon to re-inflate. Furthermore, the UI 336 includes a parameter indicator 344 indicating a (e.g. current) biometric parameter being monitored in accordance with present principles, and an elapsed time indicator 346 indicating e.g. the time elapsed since the start of the balloon deflation, though in other instances it may indicate the total time the balloons(s) has been at least partially inflated since its initial inflation began.

Figure 17:
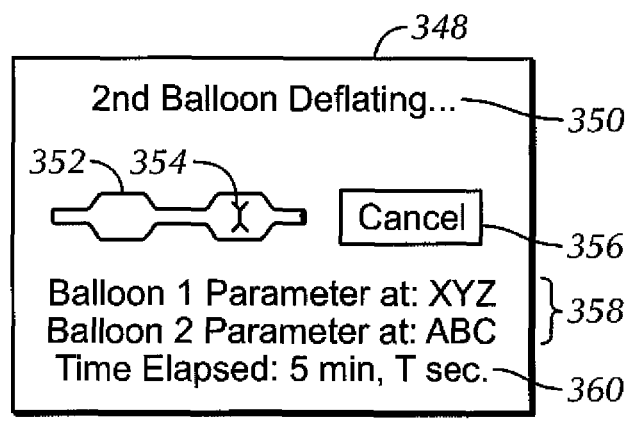

Now in reference to FIG. 17, an exemplary UI 348 is shown for indicating that a second balloon of a catheter is deflating in accordance with present principles, in this case the distal balloon, as represented by indicator 350. Also shown is a representation 352 of a catheter that includes bi-directional arrows 354 similar to the arrows 340 described above in that they indicate that a balloon is deflating, in this case the second, distal balloon. A cancel selector element 356 is also shown for canceling and/or stopping deflation of at least the second balloon to thus maintain an at least partial inflation of the balloon, but may also be selectable for canceling and/or stopping deflation of both balloons and/or re-inflating one or both balloons. Furthermore, the UI 348 includes plural parameter indicators 358 indicating respective (e.g. current) biometric parameters being monitored in accordance with present principles for each of the balloons (though in addition to or in lieu of the foregoing, a cumulative biometric parameter and/or overall biometric parameter may be presented). Also shown is an elapsed time indicator 360 indicating e.g. the time elapsed since the start of the second balloon deflation, though in other instances it may indicate the total time the balloon(s) has been at least partially inflated since its initial inflation began.

Figure 18:
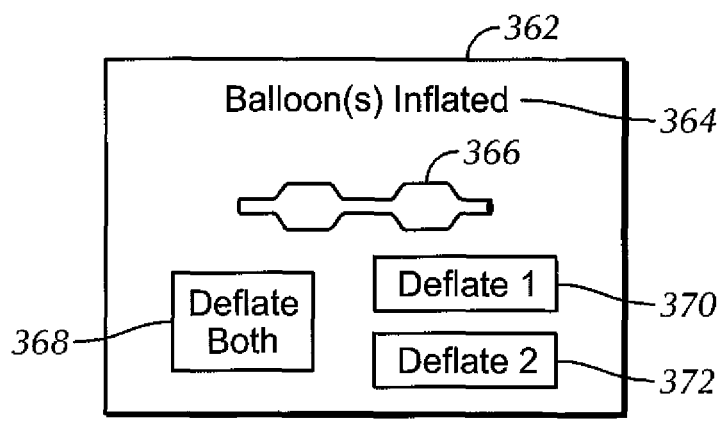

Turning now to FIG. 18, a UI 362 is shown indicating that both the proximal and distal balloons of a catheter in accordance with present principles are inflated, as represented by indicator 364 and representation 366 of a catheter showing two balloons in an (e.g. at least partial) inflated configuration. Also shown on the UI 362 is a deflate both selector element 368 selectable to cause deflation of both balloons at the same time and/or sequential deflation of the balloons. Also shown is a deflate one selector 370 selectable for deflating only the first balloon if desired, and a deflate two selector 372 selectable for deflating only the second balloon if desired. Though not shown, it is to be understood that one or more parameter bio-indicators (e.g. for the balloons) such as those described above and an elapsed time indicator such as those described above may also be presented on the UI 362 though not specifically shown in FIG. 18.

Figure 19:
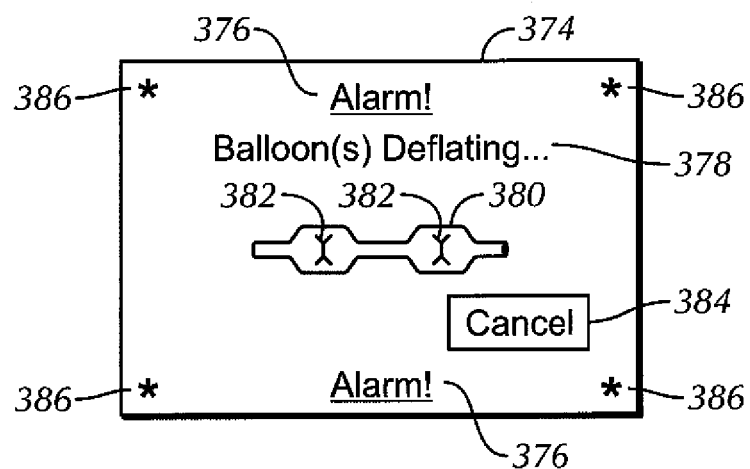

Concluding the detailed description in reference to FIG. 19, it shows an alarm UI 374 presentable when an alarm is to be provided in accordance with present principles. Thus, the UI 374 includes alarm indicators 376 on top and bottom central portions of the UI 374 and a balloon indicator 378 indicating that at least one balloon is deflating in accordance with present principles. The UI 374 also includes a representation 380 of a catheter including plural bi-directional arrows 382 that may be similar to the arrows 340 and 354 described above for indicating that the respective balloons in which they are shown as being disposed are deflating. In addition, the UI 374 includes a cancel selector element 384 selectable to cancel deflation of one or both balloons, though in other embodiments it is understood to be selectable merely to cause e.g. an audible alarm presented along with the UI 374 to cease sounding and/or to cause the UI 374 to no longer be presented on the display on which it is presented while nonetheless still deflating the balloons. Addressing simultaneous inflation of the balloons described herein, it is to be understood that in accordance with present principles, one balloon may be inflated while the other simultaneously deflated. Last, note that in exemplary embodiments stars 386 or other suitable icons indicating an alarm (such as e.g. alarm clock icons) may be presented on or proximate to corners of the UI 374 to further indicate an alarm is occurring.

Regarding any/all of the UIs described above, it is to be understood that these UIs may include a total maximum or optimal inflation time, as well as maximum and minimum (e.g. optimal) biometric parameters. Furthermore, different times can be indicated on the UIs for each balloon (from the start of inflation of each balloon). Indeed, the UI elements described above (as well as the catheter system component and logic steps) may be combined, changed, and rearranged and thus the exemplary figures above are not to be construed as limiting on the claims (e.g., a logic step in accordance with present principles may be added to one figure though not specifically shown in that particular figure or shown at a different point in the logic than where it is to be added). Also, note that thresholds may be used in accordance with present principles such that, e.g., determinations are made based on biometric parameter and/or time thresholds being met.

Without reference to any particular figure, it is to be understood that the procedures and determinations detailed in U.S. application Ser. No. 12/639,901 (U.S. Pat. No. 8,137,375), incorporated herein by reference, may be incorporated into the logic discussed herein. For example, balloon inflation may be maintained and adjusted under control of a processor so that cerebral blood flow is regulated and maintained under varying blood flow conditions.

Before concluding, it is to be understood that the inflation times and rates described herein can be different lengths of time and inflation rates in exemplary embodiments where, e.g. one balloon is inflated and then another is inflated. Addressing simultaneous inflation of the balloons described herein, it is to be understood that in accordance with present principles, one balloon may be inflated while the other simultaneously deflated. Also note that blood flow rate in accordance with present principles may be measured at various portions of the body if it is not based on cardiac output as described herein. Further still, note that fluoroscopic dye can be used in accordance with present principles (e.g. inserted into an artery/blood stream) to detect blood flow (e.g., verifying blood flow reversal) and accordingly blood flow may be a biometric parameter in accordance with present principles determined at least in part on (e.g. detection of) flow of fluoroscopic dye. Addressing simultaneous inflation of the balloons described herein, it is to be understood that in accordance with present principles, one balloon may be inflated while the other simultaneously deflated.

In addition to the foregoing, more than two balloons may be used in some instances (e.g., three) and may be controlled in accordance with the principles set forth herein. Further note that occlusion or construction of e.g. an artery using proximal and distal balloons in accordance with present principles may but need not necessarily be full occlusion and that partial occlusion may in some instances be appropriate.

Last, note that present principles recognize that the storage mediums discussed herein may store e.g. information specific to a patient and/or a procedure performed on the patient, and that therefore the logic discussed above may incorporate such information when inflating and deflating balloons (e.g. inflate a balloon to a certain level based on a previous inflation level previously applied to that particular patient in another procedure) in accordance with present principles. For instance, the results of each procedure (e.g. inflation rates, times, levels, etc.) may be stored for review by a physician when evaluating a particular patient that has undergone the procedure.

While the particular CONTROL SYSTEM FOR ARTERIAL CATHETER is herein shown and described in detail, it is to be understood that the subject matter which is encompassed by the present invention is limited only by the claims.

What is claimed is:

1. Control system for an arterial catheter operable to selectively impede blood flow in a first artery to increase blood flow in a second artery, comprising:
   at least one computer memory accessible to at least one processor and comprising instructions which when executed by the at least one processor configure the at least one processor to execute operations comprising:
   receiving a first signal representing a physical parameter associated with a patient in whom the catheter is disposed;
   receiving a second signal representative of time;
   causing inflation of a first balloon on the catheter to impede blood flow in the first artery;
   based at least in part on the first signal satisfying a first condition, causing deflation of the first balloon;
   based at least in part on the second signal indicating elapse of a predetermined time period, causing deflation of the first balloon regardless of whether the first signal satisfies the first condition, wherein the catheter includes a second balloon and the instructions are executable for:
   inflating the second balloon;
   based at least in part on the first signal satisfying a second condition, causing deflation of the second balloon; and
   based at least in part on the second signal indicating elapse of a predetermined time period, causing deflation of the second balloon regardless of whether the first signal satisfies the second condition.

2. The system of claim 1, wherein the physical parameter includes blood pressure of the patient.

3. The system of claim 1, wherein the physical parameter includes amount of blockage of the first artery by the first balloon.

4. The system of claim 1, wherein the physical parameter includes blood flow rate through the first artery.

5. The system of claim 1, wherein the first artery is a femoral artery and the second artery is a carotid artery.

6. The system of claim 1, wherein the instructions are executable for:
   inflating the first and second balloons simultaneously with each other.

7. The system of claim 1, wherein the instructions are executable for:
   inflating the first balloon before inflating the second balloon.

8. The system of claim 7, wherein the first balloon is distal to the second balloon.

9. The system of claim 7, wherein the first balloon is proximal to the second balloon.

10. Control system for an arterial catheter operable to selectively impede blood flow in a first artery to increase blood flow in a second artery, comprising:
    at least one computer memory accessible to at least one processor and comprising instructions which when executed by the at least one processor configure the at least one processor to execute operations comprising:
    receiving a first signal representing a pressure;
    receiving a second signal representative of time;
    causing inflation of a first balloon on the catheter to impede blood flow in the first artery;
    based at least in part on the first signal satisfying a first condition, causing deflation of the first balloon; and
    based at least in part on the second signal indicating elapse of a predetermined time period, causing deflation of the first balloon regardless of whether the first signal satisfies the first condition;
    wherein the pressure includes pressure internal to the first balloon.

* * * * *